United States Patent
Moravek et al.

(10) Patent No.: US 10,055,963 B1
(45) Date of Patent: Aug. 21, 2018

(54) ON-DUTY/OFF-DUTY WORK ALTERNATION PLANNING BASED ON SENSED PHYSIOLOGICAL AND ACTIVITY PARAMETERS

(71) Applicant: HONEYWELL INTERNATIONAL INC., Morris Plains, NJ (US)

(72) Inventors: Zdenek Moravek, Rozdrojovice (CZ); David Kunes, Tisnov (CZ); Ivan Lacko, Brno (CZ)

(73) Assignee: HONEYWELL INTERNATIONAL INC., Morris Plains, NJ (US)

( * ) Notice: Subject to any disclaimer, the term of this patent is extended or adjusted under 35 U.S.C. 154(b) by 0 days.

(21) Appl. No.: 15/426,410

(22) Filed: Feb. 7, 2017

(51) Int. Cl.
- G08B 21/00 (2006.01)
- G08B 21/04 (2006.01)
- G08B 7/06 (2006.01)
- G08B 21/18 (2006.01)
- G06Q 10/06 (2012.01)

(52) U.S. Cl.
CPC ......... G08B 21/0453 (2013.01); G08B 7/06 (2013.01); G08B 21/0476 (2013.01); G08B 21/182 (2013.01); G06Q 10/06312 (2013.01)

(58) Field of Classification Search
CPC ....... A61B 5/18; B60R 25/255; B60R 25/305; B60W 50/14; G06K 9/00845; G08B 21/06; G08B 31/00
USPC ................................................ 340/575, 576
See application file for complete search history.

(56) References Cited

U.S. PATENT DOCUMENTS

| | | | |
|---|---|---|---|
| 6,807,481 B1 * | 10/2004 | Gastelum | G01C 21/3697 340/438 |
| 7,454,313 B2 | 11/2008 | Whitlow et al. | |
| 8,652,041 B2 | 2/2014 | Moore-Ede | |
| 8,679,012 B1 * | 3/2014 | Kayyali | A61B 5/0002 382/115 |
| 9,241,658 B2 | 1/2016 | Moore-Ede | |
| 2012/0068820 A1* | 3/2012 | Mollicone | G06F 21/00 340/5.82 |
| 2012/0075119 A1 | 3/2012 | Dorneich et al. | |
| 2015/0223743 A1 | 8/2015 | Pathangay et al. | |

FOREIGN PATENT DOCUMENTS

WO    2009066109 A1    5/2009

OTHER PUBLICATIONS

Extended EP Search Report for Application No. 18154558.3 dated Jun. 18, 2018.

* cited by examiner

Primary Examiner — Mark Rushing
(74) Attorney, Agent, or Firm — Lorenz & Kopf, LLP (57) ABSTRACT

A system and method for alerting an on-duty operator of the need to transfer operational control to an off-duty operator includes processing first and second physiological and activity data from the on-duty operator and the off-duty operator, respectively. The processor compares the fatigue state of the on-duty operator to a predetermined fatigue state threshold, and the rest state of the off-duty operator to a predetermined rest state threshold. The processor will generate an alert signal indicating that the on-duty operator should transfer operational control to the off-duty operator when (i) the fatigue state of the on-duty operator exceeds the predetermined fatigue state threshold or (ii) the rest state of the off-duty operator exceeds the predetermined rest state threshold.

14 Claims, 4 Drawing Sheets

ON-DUTY/OFF-DUTY WORK ALTERNATION PLANNING BASED ON SENSED PHYSIOLOGICAL AND ACTIVITY PARAMETERS

TECHNICAL FIELD

The present invention generally relates to on-duty/off-duty work alternation planning, and more particularly relates to on-duty/off-duty work alternation planning based on sensed physiological and activity parameters.

BACKGROUND

There are many working environments in which teams of coworkers alternate between on-duty status (actively performing tasks) and off-duty status (resting and/or sleeping). For example, flight crews on long-haul flights, flight crews performing several shorter flights per day, truck drivers, ship crews, medical personnel, emergency response services, surveillance teams (e.g., power plants, border control, and security), firefighters, and military personnel are subject to such alternating work cycles.

As is generally known, planning alternations between on- and off-duty statuses can affect team performance. The quality of rest/sleep in the off-duty status depends not only on length of the rest/sleep, but in great part on when the rest/sleep ends. For example, the untimely waking of off-duty personnel may spoil up to one hour of sleep. This can, in some instances, be a significant fraction of rest/sleep allocated to the off-duty personnel before alternating back to on-duty status. As a result, the person may start their on-duty period in a drowsy state, and with reduced vigilance. This can lead to the person making unintentional errors.

Current work alternation practice tends toward relatively short on-duty and off-duty times. The alternations are pre-planned, with substantially regular intervals, and with only a limited number of allowed on-duty periods. For example, truck drivers may be required to alternate at least every 4.5 hours, and may be allowed only three on-duty periods per day. For longer shifts, the number of persons in the team may be extended. In some instances, work alternation scheduling utilizes flexible planning, where time awake or the time-of-day are taken into account to schedule rest/duty periods.

While generally safe and effective, each of the above-described work alternation scheduling approaches suffer certain drawbacks. For example, these approaches do not account for individual characteristics and modifications due to non-normal conditions, e.g. illness, suboptimal sleep in previous days, overall fatigue, difficult duty period etc. These approaches are fixed or pre-planned unless team members agree on a change, but the agreement must still be made in advance to be efficient. These approaches do not reflect the real-time state of the on-duty person. For example, the on-duty person may be able to continue to perform at a high-level beyond the agreed-upon alternation time or, alternatively, may exhibit degraded performance well before the agreed-upon alternation time.

Hence, there is a need for a system and method for planning and executing on-duty/off-duty work alternation that account for individual characteristics and modifications due to non-normal conditions, are not necessarily fixed or pre-planned, and reflect the real-time state of both the on-duty and off-duty persons. The present invention addresses at least these needs.

BRIEF SUMMARY

This summary is provided to describe select concepts in a simplified form that are further described in the Detailed Description. This summary is not intended to identify key or essential features of the claimed subject matter, nor is it intended to be used as an aid in determining the scope of the claimed subject matter.

In one embodiment, a processing system for alerting an on-duty operator of the need to transfer operational control to an off-duty operator includes a processor. The processor is configured to receive first physiological and activity data from the on-duty operator, where the first physiological and activity data are indicative of fatigue state of the on-duty operator. The processor is also configured to receive second physiological and activity data from the off-duty operator, where the second physiological and activity data are indicative of rest state of the off-duty operator. The processor compares the fatigue state of the on-duty operator to a predetermined fatigue state threshold, and compares the rest state of the off-duty operator to a predetermined rest state threshold. The processor generates an alert signal indicating that the on-duty operator should transfer operational control to the off-duty operator when (i) the fatigue state of the on-duty operator exceeds the predetermined fatigue state threshold or (ii) the rest state of the off-duty operator exceeds the predetermined rest state threshold.

In another embodiment, a system for alerting an on-duty operator of the need to transfer operational control to an off-duty operator includes a first set of sensors, a second set of sensors, an alert generator, and a processor. The first set of sensors is disposed at least adjacent to the on-duty operator and is configured to supply first physiological and activity data, where the first physiological and activity data indicative of fatigue state of the on-duty operator. The second set of sensors is disposed at least adjacent to the off-duty operator and is configured to supply second physiological and activity data, where the second physiological and activity data indicative of rest state of the off-duty operator. The alert generator is coupled to receive an alert signal and is configured, upon receipt of the alert signal, to generate an alert indicating that the on-duty operator should transfer operational control to the off-duty operator. The processor is in operable communication with the first set of sensors, the second set of sensors, and the alert generator. The processor is coupled to receive the first physiological and activity data and the second physiological and activity data and is configured, upon receipt of the first and second physiological and activity data, to: (1) determine the fatigue state of the on-duty operator; (2) determine the rest state of the off-duty operator; (3) compare the fatigue state of the on-duty operator to a predetermined fatigue state threshold; (4) compare the rest state of the off-duty operator to a predetermined rest state threshold; and (5) generate and supply the alert signal to the alert generator when (i) the fatigue state of the on-duty operator exceeds the predetermined fatigue state threshold or (ii) the rest state of the off-duty operator exceeds the predetermined rest state threshold.

In yet another embodiment, a method for alerting an on-duty operator of the need to transfer operational control to an off-duty operator includes processing, by a processor, first physiological and activity data from the on-duty operator and second physiological and activity data from the off-duty operator, where the first physiological and activity data are indicative of fatigue state of the on-duty operator and the second physiological and activity data are indicative of rest state of the off-duty operator. The processor compares the fatigue state of the on-duty operator to a predetermined fatigue state threshold, and the rest state of the off-duty operator to a predetermined rest state threshold. The processor is used to generate an alert signal indicating that the on-duty operator should transfer operational control to the off-duty operator when (i) the fatigue state of the on-duty operator exceeds the predetermined fatigue state threshold or (ii) the rest state of the off-duty operator exceeds the predetermined rest state threshold.

Furthermore, other desirable features and characteristics of the work alternation planning system and method will become apparent from the subsequent detailed description and the appended claims, taken in conjunction with the accompanying drawings and the preceding background.

BRIEF DESCRIPTION OF THE DRAWINGS

The present invention will hereinafter be described in conjunction with the following drawing figures, wherein like numerals denote like elements, and wherein.

DETAILED DESCRIPTION

The following detailed description is merely exemplary in nature and is not intended to limit the invention or the application and uses of the invention. As used herein, the word "exemplary" means "serving as an example, instance, or illustration." Thus, any embodiment described herein as "exemplary" is not necessarily to be construed as preferred or advantageous over other embodiments. All of the embodiments described herein are exemplary embodiments provided to enable persons skilled in the art to make or use the invention and not to limit the scope of the invention which is defined by the claims. Furthermore, there is no intention to be bound by any expressed or implied theory presented in the preceding technical field, background, brief summary, or the following detailed description.

Figure 1:
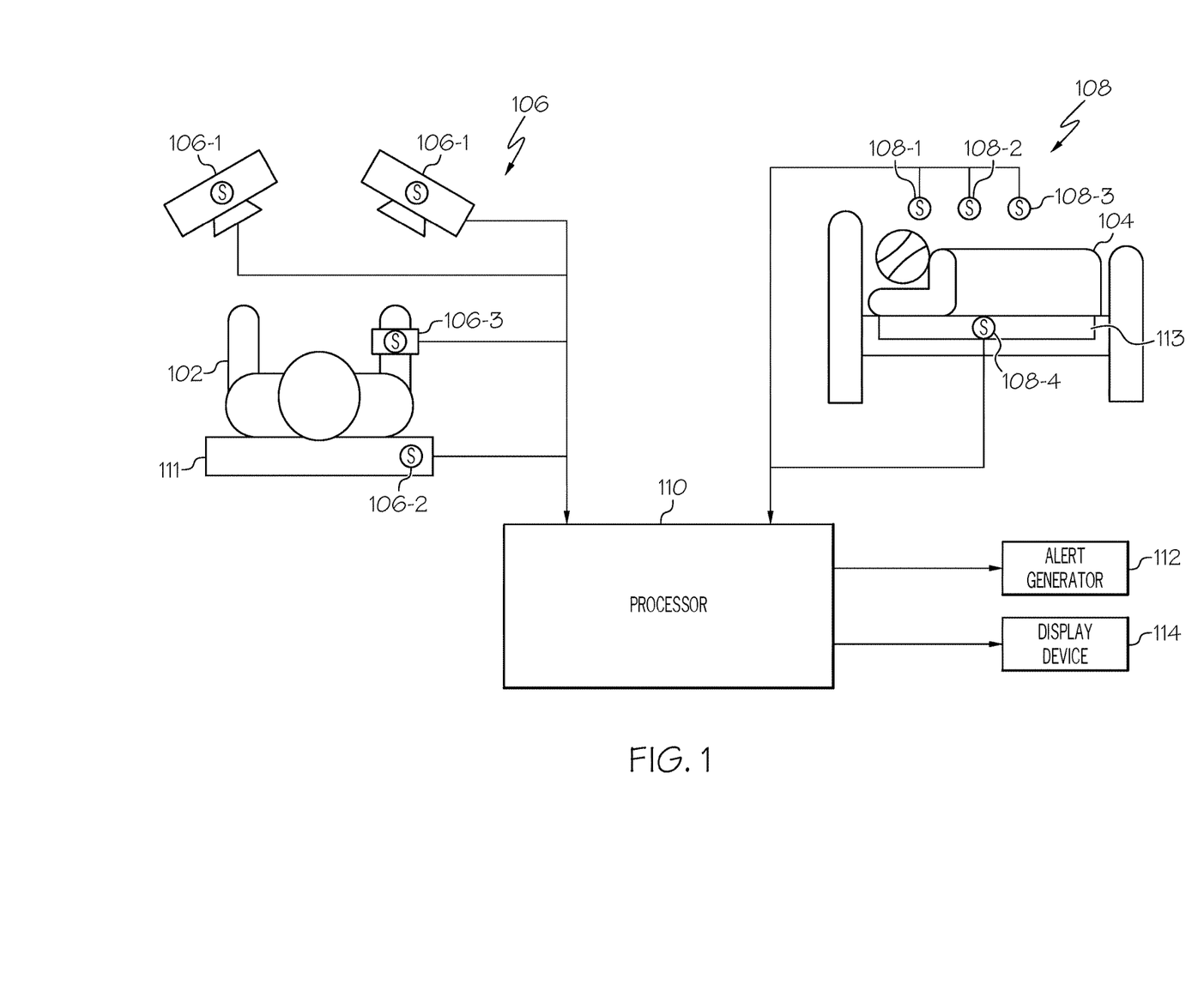
FIG. 1 depicts a functional block diagram of a system that plans work alternation.

Referring to FIG. 1, a functional block diagram of a system 100 that plans work alternation, by alerting an on-duty operator 102 of the need to transfer operational control to an off-duty operator 104, is depicted. Before describing the depicted system 100 in more detail, it is noted that, for clarity and ease of description, only one on-duty operator 102 and one off-duty operator 104 are depicted. It will be appreciated, however, that the system 100 can be implemented for plural on-duty operators 102 and/or plural off-duty operators 104.

The depicted system 100 includes a first set of sensors 106, a second set of sensors 108, and a processor 110. The first set of sensors 106 includes one or more first sensors (e.g., 106-1, 106-2, 106-3) that are disposed on, or at least adjacent to, the on-duty operator 102. The one or more first sensors are each configured to supply first physiological and activity data that are indicative of the fatigue state of the on-duty operator. The second set of sensors 108 includes one or more second sensors (e.g., 108-1, 108-2, 108-3, 108-4) that are disposed on, or at least adjacent to, the off-duty operator 102. The one or more second sensors are each configured to supply second physiological and activity data that are indicative of the rest state of the off-duty operator.

Before proceeding further, it is noted that the term fatigue generally refers the physiological state of a person that is characterized by reduced mental or physical performance capability that can impair the person's alertness and ability to operate a system or perform duties. The term rest generally refers to the physiological state of a person that is characterized by minimal functional and metabolic activities (both physical and mental). Moreover, the terms "fatigue state" and the "rest state," as used herein, each refer to a numerical value or a multidimensional parameter that corresponds to a measure of fatigue of the on-duty person 102 and a measure of rest the off-duty person 104, respectively.

Returning now to the description, it will be appreciated that the number and type of sensors that comprise the first set of sensors 106 may vary. In the depicted embodiment, however, the first set of sensors 106 includes one or more video sensors 106-1, one or more seat load sensors 106-2, and one or more electrocardiogram (ECG) sensors 106-3. In other embodiments, the first set of sensors 106 may also include inertial sensors, electro-dermal sensors, and eye tracking sensors, just to name a few non-limiting examples.

The one or more video sensors 106-1 are disposed adjacent to the on-duty operator 102 and detect, for example, various facial features and bodily movements of the on-duty operator 102. These facial features may vary, but include, for example, one or more of eyelid movements, eye movements, gaze direction, mouth morphology, and facial expressions, just to name a few. The one or more seat load sensors 106-2 are disposed within the on-duty operator's seat 111 and detect, for example, the posture state and in-seat movements of the on-duty operator 102. The one or more ECG sensors 106-3 are disposed on the on-duty operator 102 and detect the heart rate of the on-duty operator 102. It is known that various facial features, body and facial movements, posture, in-seat activity, and heart rate can all be correlated to, and used to provide a measure of, the fatigue state of a person, such as the on-duty operator 102.

It will be appreciated that the number and type of sensors that comprise the second set of sensors 108 may also vary. In the depicted embodiment, however, the second set of sensors 108 includes one or more electroencephalogram (EEG) sensors 108-1, one or more electrooculogram (EOG) sensors 108-2, one or more inertial sensors 108-3, and one or more rest surface load sensors 108-4. In other embodiments, the second set of sensors 108 may also include electrocardiogram sensors, breathing sensor, and video sensors, just to name a few non-limiting examples.

The one or more EEG sensors 108-1 sensors are disposed on the off-duty operator 104 and detect, for example, the brain wave activity of the off-duty operator's brain. The one or more EOG sensors 108-2 are also disposed on the off-duty operator 104 and detect, for example, eye movements of the off-duty person 104. The one or more inertial sensors 108-3 are disposed on the off-duty operator 104 and detect, for example, bodily movements of the off-duty operator 104. The one or more rest surface load sensors 108-4 are disposed within the off-duty operator's resting surface 113 (e.g., bed) and detect, for example, movements of the off-duty operator 104. It is known that brain wave activity, eye movement, and bodily movement can all be used to measure a person's sleep duration, sleep phase, and time in (or since) a particular sleep phase. These factors, as is also known, can be correlated to, and used to provide a measure of, the rest state of a person, such as the off-duty operator 104.

Figure 2:
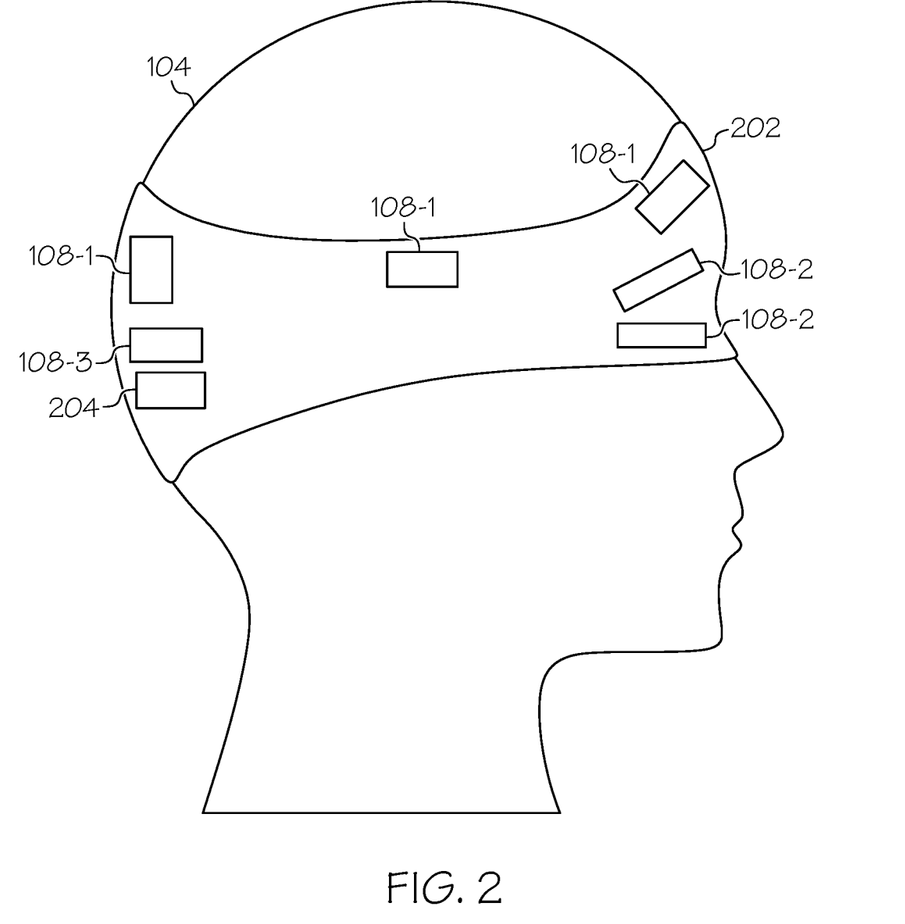
FIG. 2 depicts one embodiment of a device, wearable on the head of a user, that includes a plurality of sensors.

As may be appreciated, disposing a plurality of sensors, such as the second set of sensors 108, on a person can potentially cause discomfort and adversely impact the person's rest state. Thus, in some embodiments, such as the one depicted in FIG. 2, the second set of sensors 108 is coupled to a flexible substrate 202. The flexible substrate 202, which may be formed of any one of numerous flexible or elastic materials, is preferably configured to be worn on the head of the off-duty operator 104. It the particular embodiment depicted in FIG. 2, the flexible substrate 202 is configured as an elastic blindfold that has the various second sensors 108-1, 108-2, 108-3 disposed on or embedded therein. As FIG. 2 depicts, the flexible substrate 202 may also include a communication module 204, which may be used to communicate, using any one of numerous wired or wireless techniques, with the processor 110.

Returning now to FIG. 1, the processor 110 is in operable communication, using any one of numerous wired or wireless techniques, with the first set of sensors 106 and the second set of sensors 108. The processor 110 receives the first physiological and activity data from the first set of sensors 106, and the second physiological and activity data from the second set of sensors 108. The processor 110 is configured, upon receipt of the first and second physiological and activity data, to determine both the fatigue state of the on-duty operator 102 and the rest state of the off-duty operator 104. As noted previously, various known techniques are available and can be implemented in the processor 110 to process the received data and determine the fatigue and rest states.

The processor 110 is also configured, upon determining the fatigue and rest states, to compare the determined fatigue state of the on-duty operator 102 to a predetermined fatigue state threshold, and to compare the determined rest state of the off-duty operator 104 to a predetermined rest state threshold. As noted previously, fatigue state and the rest state each refer to a numerical value or a multidimensional parameter that corresponds to a measure of fatigue and a measure of rest, respectively. Thus, the predetermined fatigue state threshold and predetermined rest state threshold also are each a predetermined numerical value or multidimensional parameter.

The processor 110 is further configured to, in response to the above-noted comparisons, selectively generate and supply an alert signal. The alert signal, which is supplied to an alert generator 112 that is in operable communication with the processor 110, indicates that the on-duty operator 102 should transfer operational control to the off-duty operator 104. Thus, the processor 110 generates the alert signal at least when the fatigue state of the on-duty operator 102 exceeds the predetermined fatigue state threshold or the rest state of the off-duty operator 104 exceeds the predetermined rest state threshold.

The alert generator 112 is coupled to receive the alert signal from the processor 110 and is configured, upon receipt of the alert signal, to generate an alert indicating that the on-duty operator 102 should transfer operational control to the off-duty operator 104. It will be appreciated that the alert generator may be implemented using any one of more types of known alert generating devices, and may thus generate the alert using any one or more known techniques. For example, the alert generator may be configured to generate one or more of an audible alert, a visual alert, and/or a haptic alert. Regardless of the type of alert that is generated, in some embodiments the alert generator 112 is disposed near the on-duty operator 102, who is then responsible, in response to the alert, to summon the off-duty operator 104 to assume on-duty responsibilities. In other embodiments, the alert generator 112 may be disposed near the off-duty operator 104, who is then responsible, in response to the alert, to assume on-duty responsibilities from the on-duty operator 102. In still other embodiments, multiple alert generators 112 may be included, with one each disposed adjacent to the on-duty and off-duty operators 102, 104.

In many operating environments, regulatory or other requirements dictate predefined minimum and maximum time lengths. These requirements may need to be respected. Thus, at least in some embodiments, the processor 110 may also be configured to generate and supply the alert signal when the on-duty operator 102 has been on-duty for a predefined threshold time length. In these embodiments, the processor 110 is additionally configured to track the length of time the on-duty operator 102 has been on-duty, and compare the length of time to the predefined threshold time length. When the length of time exceeds the predefined threshold time length, the processor 110 will generate the alert signal.

As FIG. 1 also depicts, the system 100, at least in some embodiments, may also include a display device 114. The display device 114, which may be implemented using any one of numerous known display technologies, is in operable communication with the processor 110, and is responsive to commands from the processor 110 to render various images. In these embodiments, the processor 110 is configured to command the display device 110 to continuously render the planned shift change time for the on-duty and off-duty operators 102, 104. As may be appreciated, the rendered shift change time may vary based on the fatigue state of the on-duty operator 102 and the rest state of the off-duty operator 104. One example of how the planned shift change time for the on-duty and off-duty operators 102, 104 may be rendered is depicted in FIGS. 3 and 4, and with reference thereto will now be described.

Figure 3:
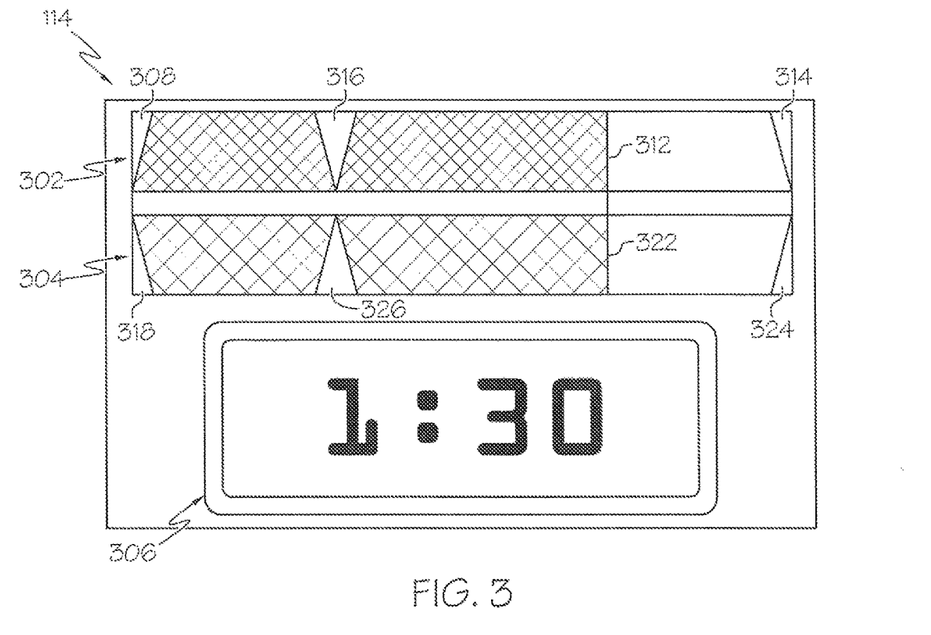
FIGS. 3 and 4 depict one embodiment of how a planned shift change time for on-duty and off-duty operators may be rendered on a display device.
Figure 4:
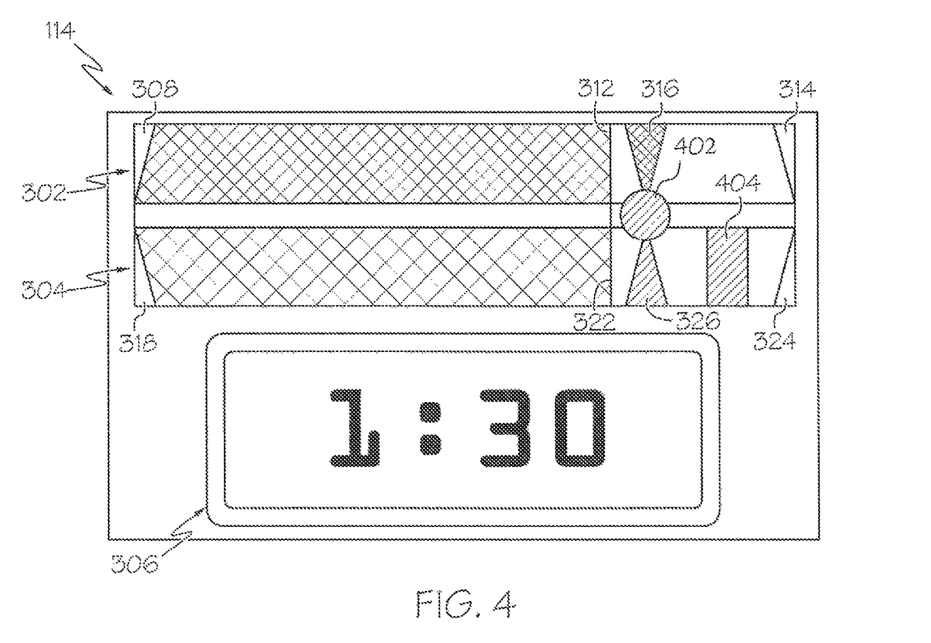

In the depicted embodiment, and with reference first to FIG. 3, the display device 114 renders at least three different image fields. These images include a duty status image field 302, a rest status image field 304, and a current time field 306. The current time field 306, as may be appreciated, displays the current time.

The duty status image field 302 includes a duty period start icon 308, a minimum duty period icon 312, a maximum duty period icon 314, and a current on-duty time icon 316. The duty period start icon 308 and the minimum duty period icon 312 are spaced apart from each other by a distance that represents the above-mentioned predefined minimum shift time length. The duty period start icon 308 and the maximum duty period icon 314 are spaced apart from each other by a distance that represents the above-mentioned predefined maximum shift time length (e.g., the predefined threshold time length). The current on-duty time icon 316 represents the current on-duty time of the on-duty operator 102 within the current shift. As may be appreciated, the current on-duty time icon 316 continuously traverses from the duty period start icon 308 toward the maximum duty period icon 314.

The rest status image field 304 includes a rest period start icon 318, a minimum rest period icon 322, a maximum rest period icon 324, and a current off-duty time icon 326. The rest period start icon 318 and the minimum rest period icon 322 are spaced apart from each other by a distance that represents the above-mentioned predefined minimum shift time length. The rest period start icon 308 and the maximum rest period icon 324 are spaced apart from each other by a distance that represents the above-mentioned predefined maximum shift time length (e.g., the predefined threshold time length). The current off-duty time icon 326 represents the current on-duty time of the on-duty operator 102 within the current shift. As may be appreciated, the current off-duty time icon 326 continuously traverses from the rest period start icon 318 toward the maximum rest period icon 324.

As may be appreciated, the current on-duty time icon 316 and the current off-duty time icon 326 will traverse together at the same rate. It will additionally be appreciated that the minimum duty period icon 312 and the minimum rest period icon 322 are aligned, and may in some embodiments be rendered as a single icon. Similarly, the duty period start icon 308 and the rest period start icon 318 are aligned, as are the maximum duty period icon 314 and the maximum rest period icon 324.

After the current on-duty time icon 316 and the current off-duty time icon 326 traverse past the minimum duty period icon 312 and the minimum rest period icon 322, respectively, the current on-duty time icon 316 and the current off-duty time icon 326 may be rendered in a different color if the processor 110 determines that the on-duty operator 102 should transfer operational control to the off-duty operator 104. For example, if the fatigue state of the on-duty operator 102 indicates that he/she is too fatigued to continue, the current on-duty time icon 316 may be rendered in a first color (e.g., amber), and if the rest state of the off-duty operator 104 indicates that he/she is ready to be awakened, the current off-duty time icon 326 may be rendered in a second color (e.g., green). Both of these situations are depicted in FIG. 4.

As FIG. 4 also depicts, after predefined minimum shift time length has lapsed, and when the processor 110 determines that the on-duty operator 102 should transfer operational control to the off-duty operator 104, the processor 110 commands the display device 114 to additionally render a switch recommendation icon 402. The switch recommendation icon 402 may be variously rendered, but in the depicted embodiment it is rendered as a circle between, and overlying portions of, the current on-duty time icon 316 and the current off-duty time icon 326. Thus in addition to generating an alert via the one or more alert generators 112, the switch recommendation icon 402 will also provide an indication to the on-duty operator 102 that he/she should transfer operational control to the off-duty operator 104.

For some time after predefined minimum shift time length has lapsed, the off-duty 104 may not be ready to be awakened. However, and as FIG. 4 additionally depicts, the processor 110 may additionally command the display device 114 to additionally render a predicted wake-up time icon 404. The predicted wake-up time icon 404, when rendered, indicates a prediction of when the off-duty operator 104 will likely be ready to be awakened.

Figure 5:
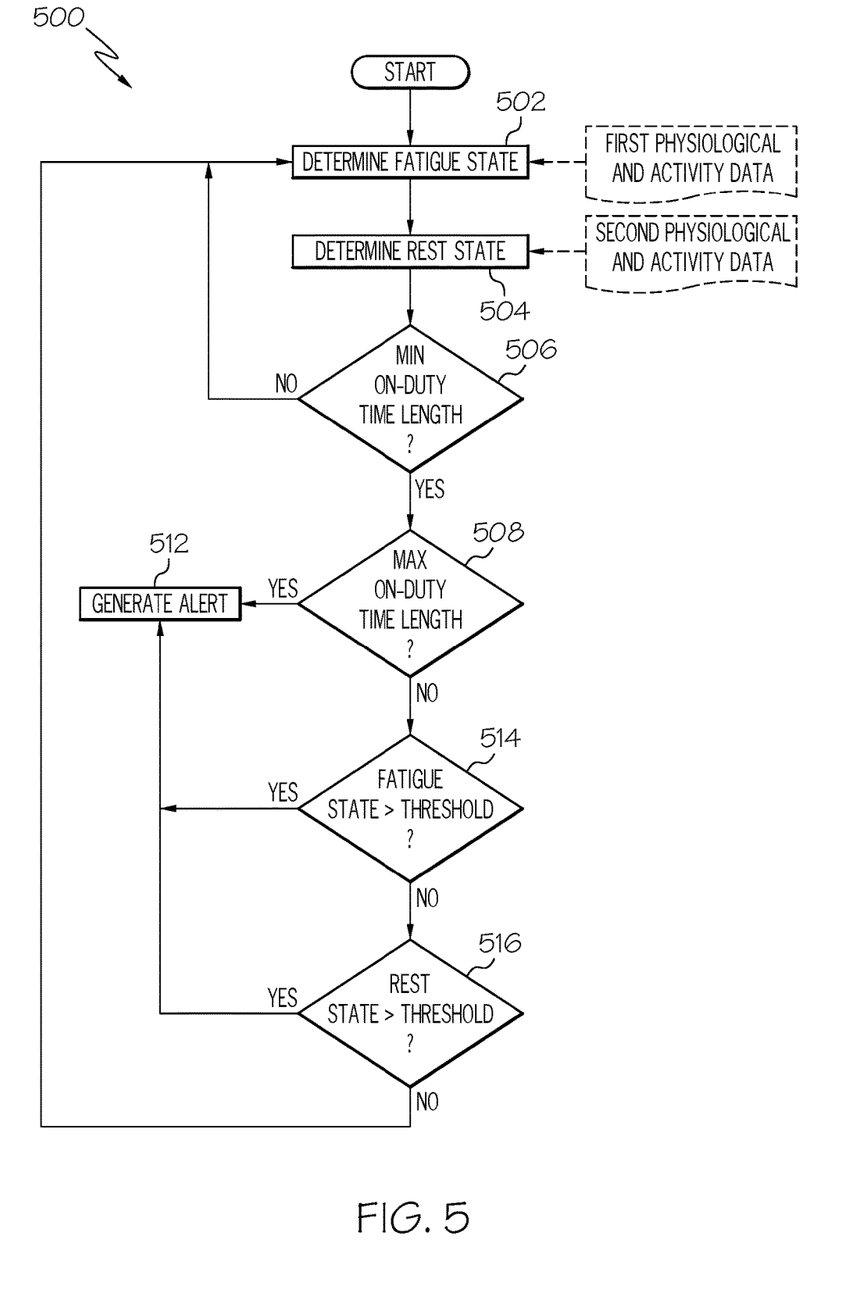
FIG. 5 depicts a process, in flowchart form, of a process implemented in the system of FIG. 1 for planning work alternation.

One embodiment of a process that the system 100 implements for planning work alternation is depicted in FIG. 5. The process, which will be described in more detail further below, continuously processes the physiological and activity data associated with the on-duty and off-duty operators 102, 104. As may be appreciated, increased activity by the on-duty operator 102 contributes to fatigue and may favor a shorter length of on-duty time. As may also be appreciated, increased activity by the off-duty operator 104 can adversely impact rest/sleep quality and may favor a longer length of off-duty. Regardless, however, and as noted above, the predefined minimum and maximum on-duty/off-duty time lengths are respected, and define a window of time within which changes in on-duty and off-duty time lengths may be varied. Within this defined window of time, the fatigue state of the on-duty operator 102 and the rest state of the off-duty operator 104 are continuously assessed. If the rest state of the off-duty operator 104 indicates that he/she is ready to be awakened, or the fatigue state of the on-duty operator 102 indicates that he/she is too fatigued to continue, the change in rest/duty is communicated, via the alert generator 112.

The goal of the process is to wake the off-duty operator 104 when he/she is in the appropriate phase of sleep, while simultaneously reducing the on-duty time length of the on-duty operator 102 in the event the wake-up time of the off-duty operator 104 is postponed due to being in an inappropriate sleep phase. Studies have shown that the appropriate phase of sleep to wake persons is the REM phase. Waking while in the REM phase maximizes vigilance and readiness for duty. Of course, if on-duty operator 102 is already too fatigued, the off-duty operator 104 is awakened before the planned time and regardless of sleep phase.

Referring now to FIG. 5, the process 500 includes processing the first physiological and activity data to determine the fatigue state of the on-duty operator 102 (502). The second physiological and activity data is also processed to determine the rest state of the off-duty operator 104 (504). For those operating environments in which predefined minimum and maximum time lengths are dictated, the process then includes determining if the on-duty time length is within the defined window of time.

Specifically, the processor 110 determines if the on-duty operator 102 has been on duty for the minimum on-duty time length (506). If the on-duty operator 102 has not been on duty for the minimum on-duty time length, then the first and second physiological data continue to be processed (502, 504). However, if the on-duty operator 102 has been on duty for the minimum on-duty time length, then the processor determines if the on-duty operator 102 has been on duty for the maximum on-duty time length (508).

If the on-duty operator 102 has been on duty for the maximum on-duty time length, then the alert signal is generated (512), indicating that the on-duty operator 102 should transfer operational control to the off-duty operator 104. If, however, the on-duty operator 102 has not been on duty for the maximum on-duty time length, then the processor determines if the on-duty operator 102 is too fatigued to continue or the off-duty operator 104 is sufficiently rested to take over for the on-duty operator.

Specifically, the fatigue state of the on-duty operator 102 is compared to a predetermined fatigue state threshold (514), and the rest state of the off-duty operator 104 is compared to a predetermined rest state threshold (516). If the fatigue state of the on-duty operator 102 exceeds the predetermined fatigue state threshold, or the rest state of the off-duty operator 104 exceeds the predetermined rest state threshold, then the alert signal is generated (512). If neither is true, then the process repeats.

Unlike current on-duty/off-duty work alternation practice, the system and method disclosed herein exploits knowledge in neurophysiology of fatigue and sleep. The system and method monitors the fatigue state of the on-duty person using unobtrusively recorded physiological information, and rest state of the off-duty person using unobtrusively recorded physiological information. The system and method combines the physiological information from the on-duty and off-duty persons to optimize work alternation based on what the person in duty can still support and when the person in rest can be awakened.

Those of skill in the art will appreciate that the various illustrative logical blocks, modules, circuits, and algorithm steps described in connection with the embodiments disclosed herein may be implemented as electronic hardware, computer software, or combinations of both. Some of the embodiments and implementations are described above in terms of functional and/or logical block components (or modules) and various processing steps. However, it should be appreciated that such block components (or modules) may be realized by any number of hardware, software, and/or firmware components configured to perform the specified functions. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present invention. For example, an embodiment of a system or a component may employ various integrated circuit components, e.g., memory elements, digital signal processing elements, logic elements, look-up tables, or the like, which may carry out a variety of functions under the control of one or more microprocessors or other control devices. In addition, those skilled in the art will appreciate that embodiments described herein are merely exemplary implementations.

The various illustrative logical blocks, modules, and circuits described in connection with the embodiments disclosed herein may be implemented or performed with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general-purpose processor may be a microprocessor, but in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration.

The steps of a method or algorithm described in connection with the embodiments disclosed herein may be embodied directly in hardware, in a software module executed by a processor, or in a combination of the two. A software module may reside in RAM memory, flash memory, ROM memory, EPROM memory, EEPROM memory, registers, hard disk, a removable disk, a CD-ROM, or any other form of storage medium known in the art. An exemplary storage medium is coupled to the processor such that the processor can read information from, and write information to, the storage medium. In the alternative, the storage medium may be integral to the processor. The processor and the storage medium may reside in an ASIC.

In this document, relational terms such as first and second, and the like may be used solely to distinguish one entity or action from another entity or action without necessarily requiring or implying any actual such relationship or order between such entities or actions. Numerical ordinals such as "first," "second," "third," etc. simply denote different singles of a plurality and do not imply any order or sequence unless specifically defined by the claim language. The sequence of the text in any of the claims does not imply that process steps must be performed in a temporal or logical order according to such sequence unless it is specifically defined by the language of the claim. The process steps may be interchanged in any order without departing from the scope of the invention as long as such an interchange does not contradict the claim language and is not logically nonsensical.

Furthermore, depending on the context, words such as "connect" or "coupled to" used in describing a relationship between different elements do not imply that a direct physical connection must be made between these elements. For example, two elements may be connected to each other physically, electronically, logically, or in any other manner, through one or more additional elements.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention. It being understood that various changes may be made in the function and arrangement of elements described in an exemplary embodiment without departing from the scope of the invention as set forth in the appended claims.

What is claimed is:

1. A system for alerting an on-duty operator of the need to transfer operational control to an off-duty operator, comprising:
    a first set of sensors disposed at least adjacent to the on-duty operator and configured to supply first physiological and activity data, the first physiological and activity data indicative of fatigue state of the on-duty operator;
    a second set of sensors disposed at least adjacent to the off-duty operator and configured to supply second physiological and activity data, the second physiological and activity data indicative of rest state of the off-duty operator;
    an alert generator coupled to receive an alert signal and configured, upon receipt of the alert signal, to generate an alert indicating that the on-duty operator should transfer operational control to the off-duty operator; and
    a processor in operable communication with the first set of sensors, the second set of sensors, and the alert generator, the processor coupled to receive the first physiological and activity data and the second physiological and activity data and configured, upon receipt of the first and second physiological and activity data, to:
        determine the fatigue state of the on-duty operator;
        determine the rest state of the off-duty operator;
        compare the fatigue state of the on-duty operator to a predetermined fatigue state threshold;
        compare the rest state of the off-duty operator to a predetermined rest state threshold; and
        generate and supply the alert signal to the alert generator when (i) the fatigue state of the on-duty operator exceeds the predetermined fatigue state threshold or (ii) the rest state of the off-duty operator exceeds the predetermined rest state threshold.

2. The processing system of claim 1, wherein the first set of sensors comprises:
one or more video sensors;
one or more seat load sensors; and
one or more electrocardiogram (ECG) sensors.

3. The processing system of claim 1, wherein the second set of sensors comprises:
one or more electroencephalogram (EEG) sensors;
one or more electrooculogram (EOG) sensors; and
one or more inertial sensors.

4. The processing system of claim 3, further comprising:
a flexible substrate configured to be worn on a head of the off-duty operator,
wherein the second set of sensors is coupled to the flexible substrate.

5. The processing system of claim 4, wherein the flexible substrate is configured as a blindfold to be worn by the off-duty operator.

6. The processing system of claim 1, wherein the alert generator is configured to generate one or more of an audible alert, a visual alert, and a haptic alert.

7. The processing system of claim 1, wherein the processor is further configured to:
track a length of time the on-duty operator has been on-duty;
compare the length of time to a predefined threshold time length; and
generate the alert signal when the length of time exceeds the predefined threshold time length.

8. The processing system of claim 1, further comprising:
a display device in operable communication with the processor, the display device responsive to image rendering display commands to display one or more images,
wherein the processor is further configured to generate and supply image rendering display commands to the display device that cause the display device to continuously render planned shift change time for the on-duty and off-duty operators.

9. A system for alerting an on-duty operator of the need to transfer operational control to an off-duty operator, comprising:
a first set of sensors disposed at least adjacent to the on-duty operator and configured to supply first physiological and activity data, the first set of sensors comprising one or more video sensors, one or more seat load sensors, and one or more electrocardiogram (ECG) sensors, the first physiological and activity data indicative of fatigue state of the on-duty operator;
a second set of sensors disposed at least adjacent to the off-duty operator and configured to supply second physiological and activity data, the second set of sensors comprising one or more electroencephalogram (EEG) sensors, one or more electrooculogram (EOG) sensors, and one or more inertial sensors, the second physiological and activity data indicative of rest state of the off-duty operator; and
a processor in operable communication with the first set of sensors and the second set of sensors, the processor coupled to receive the first physiological and activity data and the second physiological and activity data and configured, upon receipt of the first and second physiological and activity data, to:
determine the fatigue state of the on-duty operator;
determine the rest state of the off-duty operator;
compare the fatigue state of the on-duty operator to a predetermined fatigue state threshold;
compare the rest state of the off-duty operator to a predetermined rest state threshold; and
generate and supply an alert signal indicating that the on-duty operator should transfer operational control to the off-duty operator when (i) the fatigue state of the on-duty operator exceeds the predetermined fatigue state threshold or (ii) the rest state of the off-duty operator exceeds the predetermined rest state threshold.

10. The processing system of claim 9, further comprising:
a flexible substrate configured to be worn on a head of the off-duty operator,
wherein the second set of sensors is coupled to the flexible substrate.

11. The processing system of claim 10, wherein the flexible substrate is configured as a blindfold to be worn by the off-duty operator.

12. The processing system of claim 9, further comprising:
an alert generator coupled to receive the alert signal from the processor and configured, upon receipt of the alert signal, to generate an alert indicating that the on-duty operator should transfer operational control to the off-duty operator.

13. The processing system of claim 12, wherein the alert generator is configured to generate one or more of an audible alert, a visual alert, and a haptic alert.

14. The processing system of claim 9, wherein the processor is further configured to:
track a length of time the on-duty operator has been on-duty;
compare the length of time to a predefined threshold time length; and
generate the alert signal when the length of time exceeds the predefined threshold time length.

* * * * *